(12) United States Patent  
Schoeneck

(10) Patent No.: US 8,541,238 B2  
(45) Date of Patent: Sep. 24, 2013

(54) APPARATUS AND METHODS FOR PERFORMING REAL TIME PCR IN ARRAY TAPE

(75) Inventor: Richard Jerome Schoeneck, Alexandria, MN (US)

(73) Assignee: Douglas Machine Inc., Alexandria, MN (US)

( * ) Notice: Subject to any disclaimer, the term of this patent is extended or adjusted under 35 U.S.C. 154(b) by 0 days.

(21) Appl. No.: 13/062,049

(22) PCT Filed: Sep. 9, 2009

(86) PCT No.: PCT/US2009/056338  
§ 371 (c)(1),  
(2), (4) Date: Mar. 3, 2011

(87) PCT Pub. No.: WO2010/030647  
PCT Pub. Date: Mar. 18, 2010

(65) Prior Publication Data  
US 2011/0166031 A1    Jul. 7, 2011

Related U.S. Application Data

(60) Provisional application No. 61/095,336, filed on Sep. 9, 2008.

(51) Int. Cl.  
*G01N 35/02* (2006.01)

(52) U.S. Cl.  
USPC ............... 436/44; 436/50; 436/164; 436/174; 422/66; 422/81; 422/402; 422/403; 422/420

(58) Field of Classification Search  
USPC .................. 436/44, 164, 177, 50; 422/66, 81, 422/402, 403, 420  
See application file for complete search history.

(56) References Cited

U.S. PATENT DOCUMENTS

| | | | |
|---|---|---|---|
| 2,895,807 A * | 7/1959 | Sorg et al. | 422/91 |
| 3,728,081 A * | 4/1973 | Bidanset | 422/66 |
| 5,720,923 A | 2/1998 | Haff et al. | |
| 6,284,546 B1 * | 9/2001 | Bryning et al. | 436/172 |
| 6,878,345 B1 * | 4/2005 | Astle | 422/552 |
| 7,232,547 B2 | 6/2007 | Rusch et al. | |
| 7,745,205 B2 | 6/2010 | Wittwer et al. | |
| 2006/0094108 A1 | 5/2006 | Yoder et al. | |
| 2008/0003649 A1 | 1/2008 | Maltezos et al. | |

* cited by examiner

*Primary Examiner* — Lyle Alexander  
(74) *Attorney, Agent, or Firm* — Alan Kamrath; Kamrath IP Lawfirm, P.A.

(57) ABSTRACT

A carrier tape (20) wound on and extending between first and second spools (40) rotatably mounted to a read head (12) is submerged with a detector (44) mounted on a guide mechanism (42) into a fluid thermal media in the form of water or air contained in tanks (76-79). While submerged, the carrier tape (20) can be wound from one spool (40) to another. Further, the read head (12) can be plunged multiple times in opposite directions in the fluid thermal media. The detector (44) allows readings while the carrier tape (20) and the contents carried thereby are submerged in the fluid thermal media and can be a multi-channel, time-resolving photometer measuring fluorescence with at least one channel per row of wells (30) arranged in an array.

22 Claims, 4 Drawing Sheets

APPARATUS AND METHODS FOR PERFORMING REAL TIME PCR IN ARRAY TAPE

BACKGROUND

The present invention generally relates to apparatus and methods for performing real time assays and specifically for performing real time PCR in array tape.

An endpoint assay performs a single measurement after a reaction is complete, while a real time assay performs multiple measurements during the reaction. Measuring a reaction over time is known as 'chemical kinetics' or 'reaction kinetics'. This kinetic data provides additional information about the reaction process.

The benefits of real time assays over endpoint assays are many. Chemical reactions often follow a natural exponential rate. By measuring the reaction kinetics, the exponential rate may be observed and quantified. The amount of initial reagent may be quantified based upon the kinetics. The kinetics of one reaction may be compared with a similar reaction or a standardized reaction.

Polymerase Chain Reaction (PCR) causes DNA amplification. The measure of the reaction is based upon measuring the amount of DNA in the sample. This is typically done using fluorescent probes. Some PCR chemistries incubate using a single reaction temperature, while others use multiple temperatures. When using multiple temperature incubation, ideally each strand of DNA will be limited to doubling with each thermal cycle. In the case of single temperature reactions, the DNA amplification will proceed at some rate, and measurements would be taken periodically.

Although real time assays have been performed utilizing plates and tubes, such real time assays are conventionally not performed on large scale experiments due to various factors including cost, speed, and the like.

Thus, a need exists for apparatus and methods for performing real time assays which overcome the deficiencies and shortcomings of conventional apparatus and methods of doing so.

SUMMARY

The present invention solves this need and other problems in the field of real time assays by providing, in a preferred form, apparatus and methods where the carrier and the contents carried by the carrier are simultaneously submerged in a fluid thermal media contained in a tank while the condition of the contents of the carrier undergoing a reaction is being detected by a detector.

In preferred aspects, the carrier is in the form of carrier tape including a plurality of wells and in most preferred aspects wound on and extending between first and second spools submerged and potentially plunged multiple times in the fluid thermal media while the carrier tape is being wound from one spool to another and extends over a guide mechanism carrying the detector. In most preferred aspects, the detector is a multi-channel, time-resolving photometer measuring fluorescence with at least one channel per row of wells arranged in an array.

In other aspects, the carrier and the contents carried thereby are sequentially submerged in multiple tanks containing fluid thermal media in the form of water or air under differing temperature control.

The present invention will become clearer in light of the following detailed description of illustrative embodiments of this invention described in connection with the drawings.

DESCRIPTION OF DRAWINGS

The illustrative embodiments may best be described by reference to the accompanying drawings where.

Figure 1:
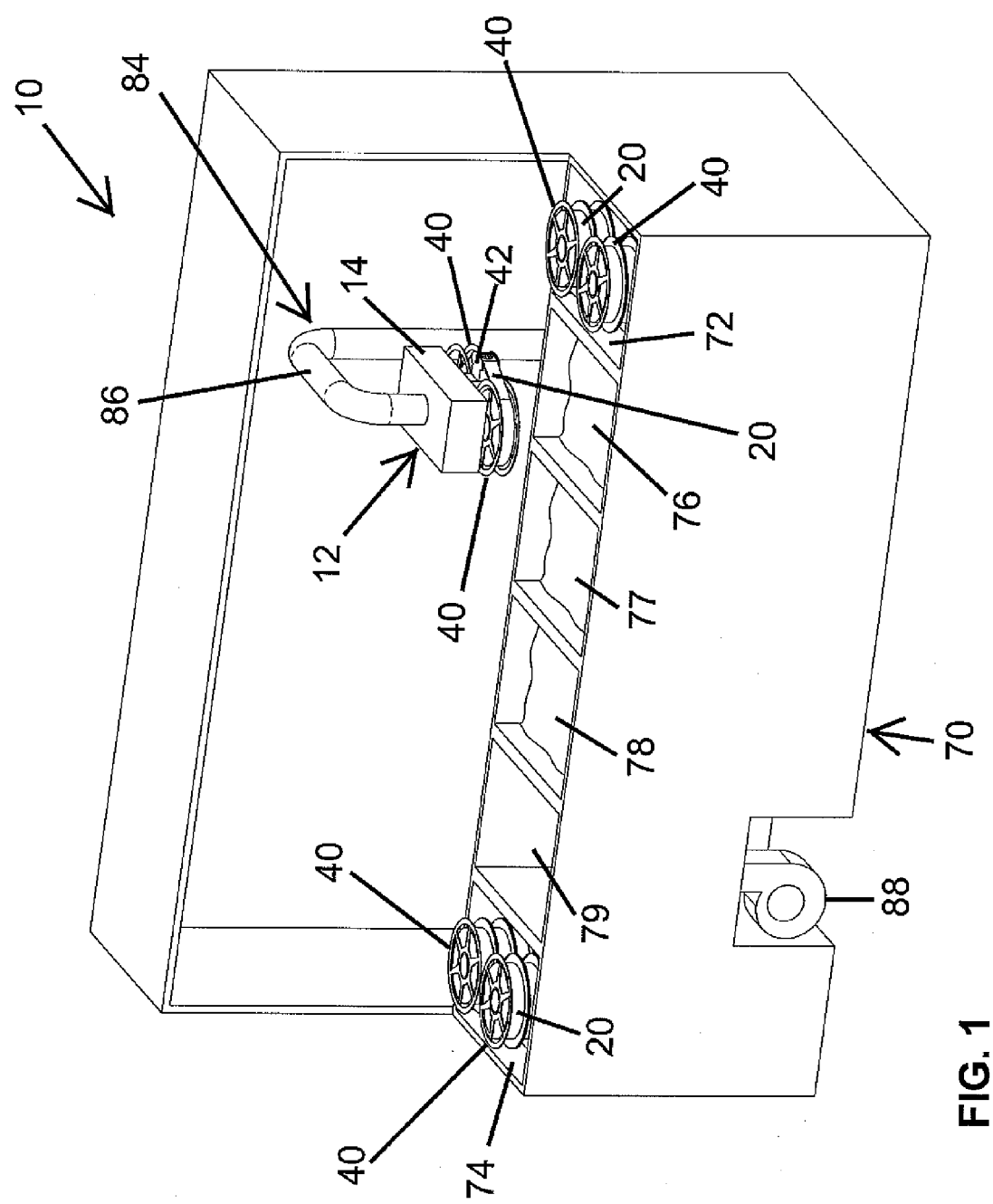
FIG. 1 shows a perspective view of an apparatus for performing real time PCR in array tape according to the preferred teachings of the present apparatus.
Figure 2:
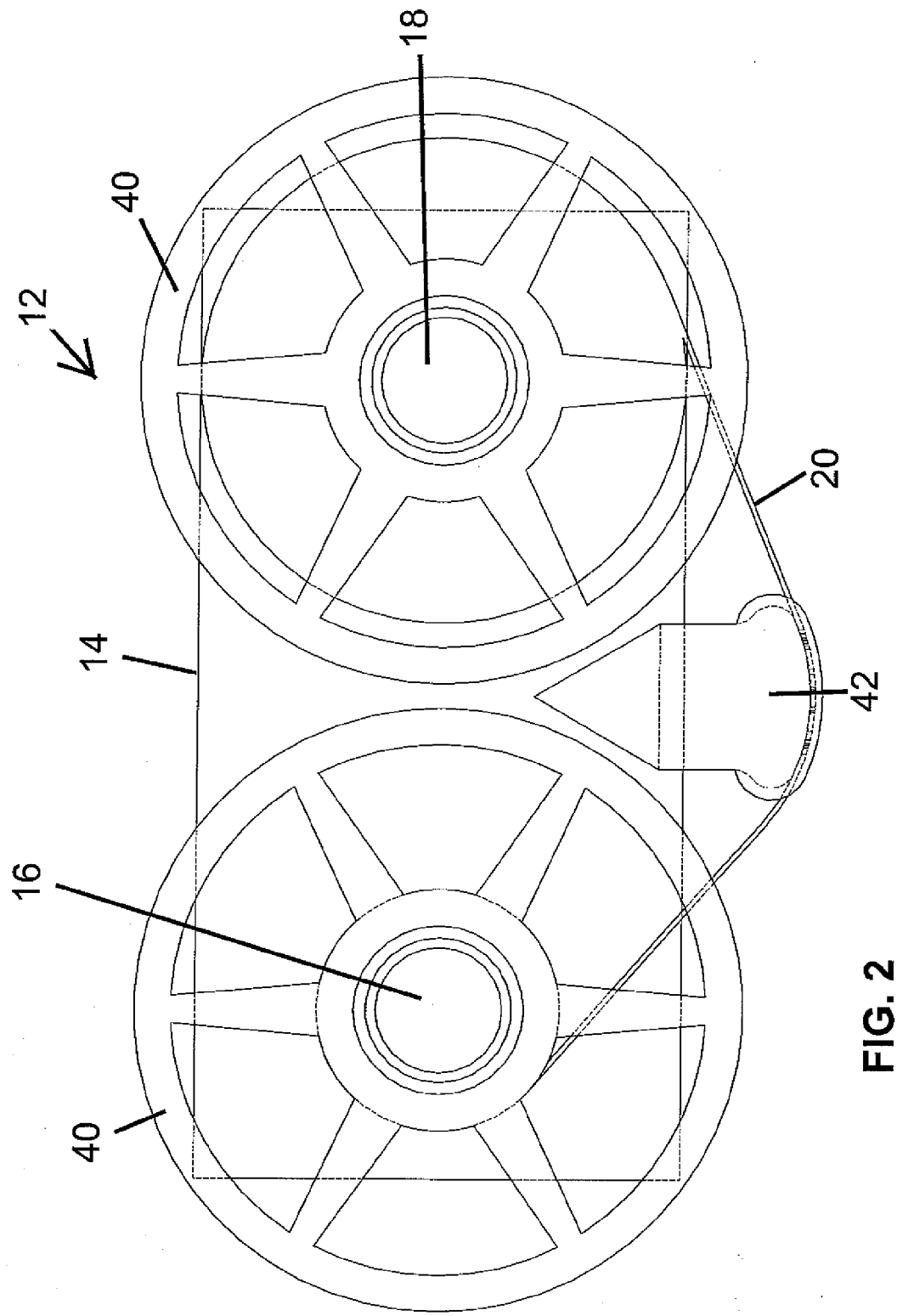
FIG. 2 shows an enlarged, partial, bottom view of the read head of the apparatus of FIG. 1.
Figure 3:
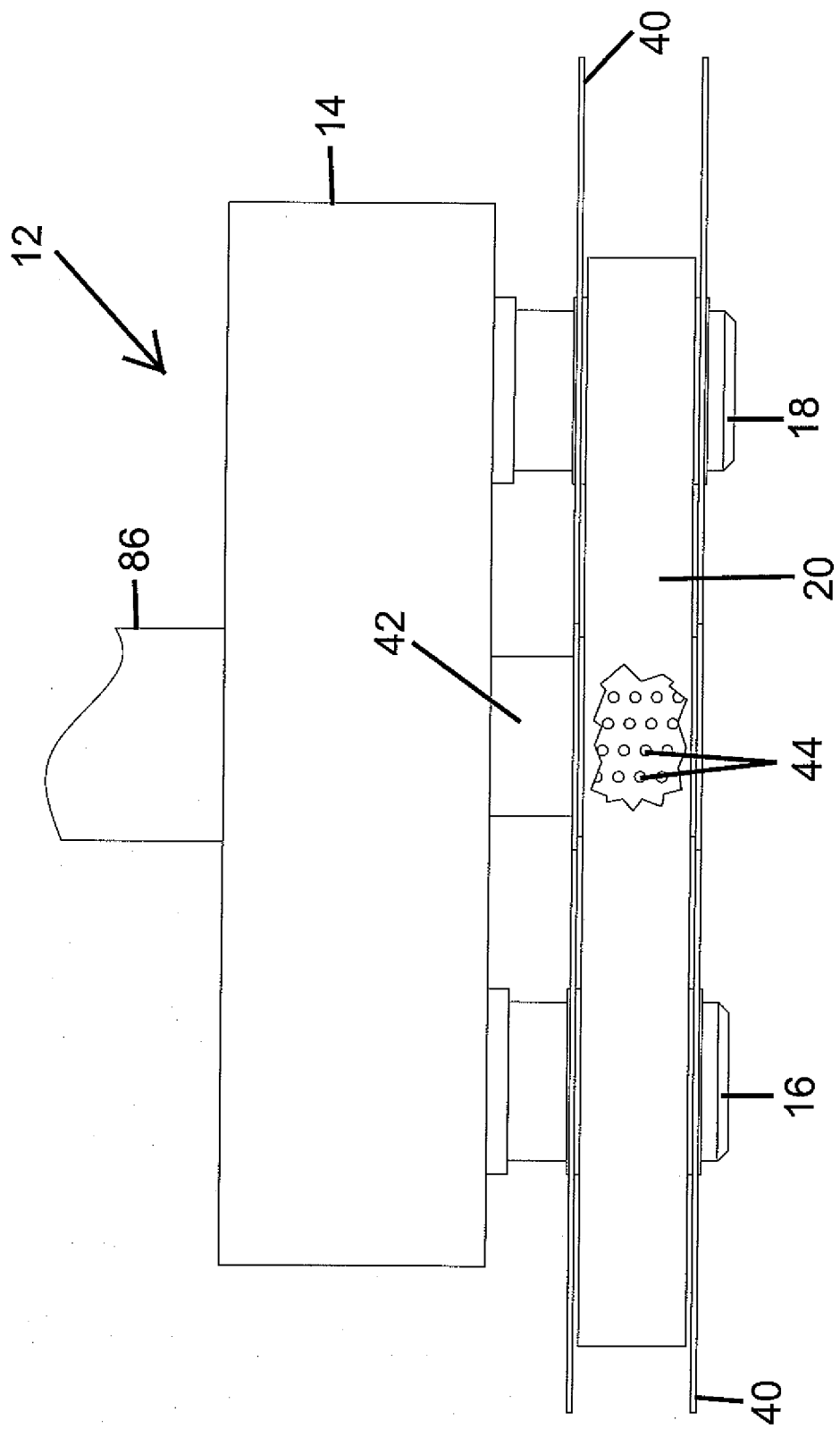
FIG. 3 shows a side view of the read head of the apparatus shown in FIG. 2 of the apparatus shown in FIG. 1, with portions of the carrier tape broken away to expose portions of the read head.
Figure 4:
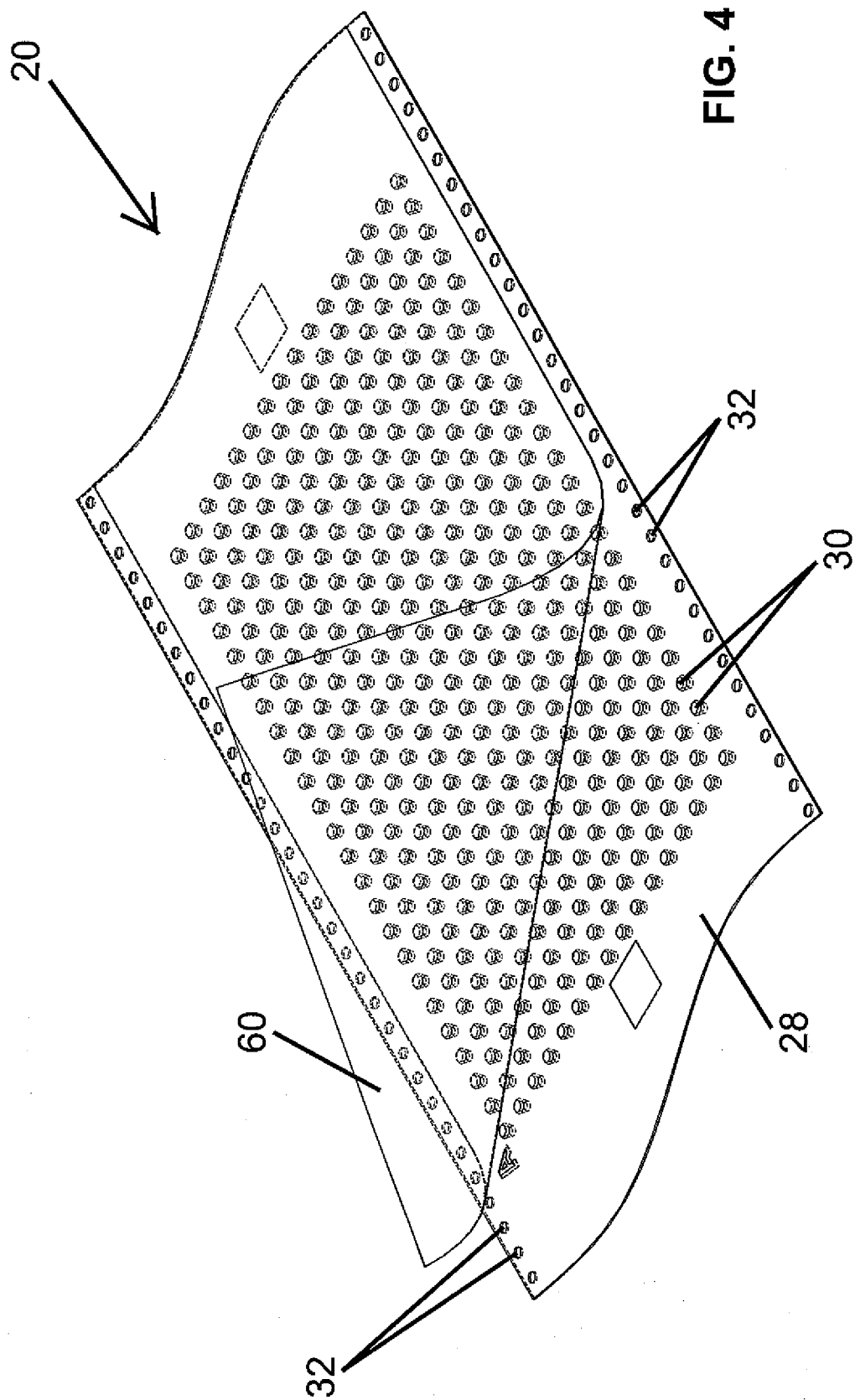
FIG. 4 shows a partial, perspective view of a carrier tape utilized in the apparatus of FIG. 1, with the seal tape rolled back to expose the upper surface of the carrier tape.

All figures are drawn for ease of explanation of the basic teachings of the present invention only; the extensions of the figures with respect to number, position, relationship, and dimensions of the parts to form the preferred embodiments will be explained or will be within the skill of the art after the following description has been read and understood. Further, the exact dimensions and dimensional proportions to conform to specific force, weight, strength, and similar requirements will likewise be within the skill of the art after the following description has been read and understood.

Where used in the various figures of the drawings, the same numerals designate the same or similar parts. Furthermore, when the terms "top", "bottom", "first", "second", "upper", "front", "back", "height", "width", "length", "end", "horizontal", "vertical", and similar terms are used herein, it should be understood that these terms have reference only to the structure shown in the drawings as it would appear to a person viewing the drawings and are utilized only to facilitate describing the illustrative embodiments.

DESCRIPTION OF THE PREFERRED EMBODIMENTS

An apparatus for performing real time PCR in an array tape according to preferred methods of the present invention is shown in the drawings and generally designated 10. In the most preferred form, apparatus 10 is utilized in connection with a carrier including regions containing contents for which a condition is desired to be detected while undergoing a reaction. Such contents include various biological and/or chemical substances which undergo reactions under different temperatures. In the most preferred form, the carrier is shown as a carrier tape 20 such as disclosed in U.S. Pat. No. 6,878,345, which is hereby incorporated herein by reference. Generally, carrier tape 20 includes a substrate 28 which is processed to emboss therein a plurality of wells 30 in specific patterns to hold liquid. In the most preferred form, wells 30 are located in an array having a plurality of rows and a plurality of columns. Further, the contents within wells 30 of carrier tape 20 can be sealed therein by a seal layer 60. It should be appreciated that the carrier can be of a variety of types and forms and is not limited to the type shown and described herein. In this regard, the number of regions containing contents, the pattern of wells 30, the shape of wells 30 and/or even the existence of wells 30 can be varied according to a function of the application according to the teachings of the present invention.

In the preferred form of carrier shown, a plurality of sprocket drive holes 32 is provided along each edge of substrate 28 and parallel to and spaced from the plurality of columns when wells 30 are located in an array. Sprocket drive holes 32 are precision punched to maintain a uniform spacing. This permits tractor driving carrier tape 20 for transport. Sprocket drive holes 32 also create a positional relationship to define any location on carrier tape 20 to provide recall to any selected well 30 on the carrier tape 20. However, it can be appreciated that other methods for tracking movement of carrier tape 20 can be utilized according to the teachings of the present invention. For example, bar codes placed between arrays or patterns of wells 30 can be read. Likewise, position feedback from spindles 16 and 18 can be utilized in conjunction with other detectors. Similarly, optical scanning can be utilized according to the teachings of the present invention such as observing arrays or patterns of wells 30, spaces between arrays or patterns of wells 30, wells 30 within arrays or patterns which are empty, the number of columns in an array of wells 30, or the like.

Generally, apparatus 10 according to the teachings of the present invention includes a read head 12 having a body 14. First and second spindles 16 and 18 extend from a lower surface of body 14 in the most preferred form shown and are rotatable about parallel, spaced axes. In the most preferred form, both spindles 16 and 18 are driven and without need for a drive intermediate spindles 16 and 18. Each of spindles 16 and 18 removably receive a spool 40 for carrier tape 20. Carrier tape 20 is wound on one or both spools 40 of spindles 16 and 18 and extends therebetween with wells 30 extending outwardly, although carrier tape 20 could be wound in an opposite direction so that wells 30 extend inwardly. Carrier tape 20 is wound from one of the spools 40 to the other of the spools 40 when spindles 16 and 18 are rotated.

Read head 12 according to the teachings of the present invention further includes a guide mechanism 42 located intermediate spindles 16 and 18 and over which seal layer 60 of carrier tape 20 passes. In the most preferred form, carrier tape 20 extends from spools 40 tangentially to guide mechanism 42, with guide mechanism 42 defining an obtuse angle in carrier tape 20 between spindles 16 and 18. In the form shown, guide mechanism 42 mounts a detector 44 for detecting a condition of carrier tape 20 and/or the contents within wells 30. In the most preferred form, detector 44 is in the form of time-resolving photometer to measure fluorescence and can be in the form of a multi-channel photometer having at least one detector channel per row of wells 30 when arranged in arrays in carrier tape 20 to eliminate physical limitations of scanning. Further, in the most preferred form, the number of channels of detector 44 is equal to and corresponds to the number of rows when wells 30 are arranged in arrays. As an example, detector 44 utilizes 16 channels for carrier tape 20 with wells 30 arranged in arrays of 384 and 32 channels for carrier tape 20 with wells 30 arranged in arrays of 1536. It should be appreciated that multi-color excitation lights suited to the various fluorescent dyes in the chemistry of the contents of wells 30 can be provided in conjunction with detector 44.

Body 14 in the preferred form is fluid sealed and includes drives for spindles 16 and 18, electronics for detector 44, and the like. It should be appreciated that the purpose of spindles 16 and 18 and spools 40 is to provide a mechanism to move carrier tape 20 past detector 44 which in one preferred form is a multi-channel reader. Furthermore, detector 44 in the preferred form shown is integrated with the tape drive in the form of spindles 16 and 18 and spools 40 such that carrier tape 20 is passed across the optical channels of detector 44. The purpose of guide mechanism 42 is to precisely align carrier tape 20 with the optical channels of detector 44 to control both depth of focus and tracking in alignment parallel to motion of carrier tape 20 in the most preferred form. However, it can be appreciated that the mechanism for moving carrier tape 20 past detector 44 can be of other forms and/or types according to the teachings of the present invention. Likewise, detector 44 can be of other forms, types and/or locations according to the condition desired to be detected according to the teachings of the present invention.

Generally, apparatus 10 as shown according to the preferred teachings of the present invention further includes an incubator 70. In particular, incubator 70 includes an inbox or load station 72 and an outbox or unload station 74. Further, incubator 70 includes a plurality of thermal media tanks 76-79 located operationally intermediate stations 72 and 74, with each tank 76-79 defining a volume having an opening. Specifically, each of tanks 76-79 contain a thermal media in the form of a fluid into which carrier tape 20 is immersed to change the temperature of carrier tape 20 and the contents carried by carrier tape 20. The thermal media contained in each of the tanks 76-79 can be at differing temperatures. The media can be in the form of water which is best for multi-temperature incubation where quick transitions between temperatures are desired, since water has a relatively high specific heat and high thermal conductivity. The media can be in the form of air which is less messy than water and is beneficial for single temperature incubation chemistry where the need for quick temperature changes is removed so the benefits of water are not required. In a preferred form, tank 76 contains hot water such as for the denaturation step for PCR in the order of 94-98 degrees Centigrade, tank 77 contains warm water such as for the extension step for PCR in the order of 78-80 degrees Centigrade, tank 78 contains cold water such as for the annealing step for PCR in the order of 50-65 degrees Centigrade, and tank 79 contains air. Any tank 76-79 such as tank 79 containing air can include a blower 88 for increasing convection. Further, each tank 76-79 should include a manner of controlling the temperature of the fluid media contained therein.

Apparatus 10 according to the teachings of the present invention includes provisions for moving the read head 12 relative to the media contained in tanks 76-79. As an example, with tanks 76-79 located in a linear row between stations 72 and 74, a Cartesian transfer mechanism 84 of the form shown can be utilized. Specifically, transfer mechanism 84 of the gantry type shown includes a U-shaped transfer arm 86 having a first leg secured to the top surface of body 14 opposite to spindles 16 and 18 and extending parallel to and intermediate the rotation axes of spindles 16 and 18. Suitable provisions are provided for moving transfer arm 86 in a vertical Z-axis motion parallel to the rotation axes of spindles 16 and 18 and in a horizontal x-axis motion perpendicular to the rotation axes of spindles 16 and 18. However, it should be appreciated that other types and forms of provisions for moving read head 12 can be utilized including a scara type with vertical Z-axis motion such as parallel to the axes of spindles 16 and 18 and a single rotary axis such as parallel to and spaced from the axes of spindles 16 and 18.

Now that the basic construction of apparatus 10 according to the teachings of the present invention has been set forth, a method of performing real time assays and, in particular, real time PCR and advantages obtained by the present invention can be highlighted. Specifically, carrier tape 20 is wound on a first spool 40 with an inner end firmly attached to first spool 40. The free end of carrier tape 20 is firmly attached to a second spool 40. First and second spools 40 are placed in load station 72, and in the preferred form, a guard is closed. There-after, read head 12 is moved to connect spindles 16 and 18 to first and second spools 40. This movement can be manually controlled or can be automatically controlled such as the result of sensing the presence of spools 40 in the load station 72.

After spools 40 are located on read head 12, read head 12 is moved to insert spools 40, guide mechanism 42, and detector 44 in the preferred form shown through the opening into the volume of one of tanks 76-79. As an example, transfer mechanism 84 can move read head 12 into tank 76 such that spools 40, carrier tape 20, guide mechanism 42, and detector 44 of the preferred form shown are spaced from the opening and extend into the fluid thermal media such as hot water located in tank 76. At that time, carrier tape 20 can be wound at high speed from one spool 40 to the other spool 40 one or more times to encourage convection currents with good contact of the thermal media with all surfaces of carrier tape 20 that otherwise might be shielded from the media due to the close spacing of the wound layers of carrier tape 20 when wound on the spools 40. Further, transfer mechanism 84 may plunge read head 12 up and down in tank 76 to encourage convection currents to pass between wound layers of carrier tape 20 when wound on spools 40, again providing for faster temperature transitions.

Detector 44 can sense the condition at any time while carrier tape 20 and the contents being carried thereby are submerged in the fluid thermal media such as while being wound between spools 40 and when the contents are located intermediate spools 40 such as when passing over guide mechanism 42. For example, detector 44 could measure fluorescence signals of the contents of wells 30 in a preferred form. For multi-temperature PCR, the reading will typically take place after the extension phase of the PCR process. It should be appreciated that detector 44 as well as carrier tape 20 and spools 40 are immersed in the fluid thermal media when the condition is being detected by detector 44 in apparatus 10 of the preferred form shown.

When the incubation period is complete for tank 76, transfer mechanism 84 can remove read head 12 from tank 76 and move it into another tank 77-79 for incubation at a second, different temperature, if desired. This process can be repeated for each of tanks 77-79 as desired. After the desired number of incubation cycles has been completed, transfer mechanism 84 can move read head 12 to unload station 74 where spools 40 with carrier tape 20 wound thereon can be removed from spindles 16 and 18. At that time, read head 12 can be moved back to load station 72. The dynamics of amplification can be analyzed per well 30 according to the data recorded in each incubation cycle.

Conventionally, there are two main physical obstacles to performing real time PCR quickly. The first obstacle is the requirement to change the temperature of many samples quickly and uniformly. Carrier tape 20 according to the teachings of the present invention is advantageous over plates and tubes due to thinner materials requiring less thermal energy. This enables an entire spool 40 of carrier tape 20 with hundreds of contents contained in addressable regions such as in arrays of wells 30 to be processed in parallel. The second obstacle is positioning each sample relative to a measuring device. Carrier tape 20 is again advantageous due to the ability to wind and feed the carrier tape 20 very quickly from spool 40 to spool 40. The multi-channel detector 44 of the most preferred form eliminates the need to raster scan a single channel reader across each column and enables feeding only the carrier tape 20 with a high speed continuous rewind motion. Specifically, utilizing apparatus 10 of the preferred form of the present invention, carrier tape 20 can be moved at 1000 mm/second. With arrays of wells 30 on 144 mm spacing, with thermal cycles typically taking 1 to 2 minutes, and with the read time for 100 arrays approximately 15 seconds, the total time per cycle is 1.5 to 2 minutes for apparatus 10 shown. As typically 15 to 20 cycles are run, the total read time for 384 wells of 100 arrays, 38,400 samples processed, is 30 to 40 minutes for apparatus 10 shown. This is at least 100 times faster than conventional systems that process one plate at a time.

Conventionally, real time PCR was not performed on large scale experiments, because it was cost prohibitive. Most labs used real time analysis for small projects and used end point assays on large projects. Because of the great speed of the tape based system, the cost per sample will be very affordable utilizing apparatus 10 and the methods according to the teachings of the present invention. Thus, labs will be able to switch over to real time analysis for all projects due to the superior real time data as compared to end point assays. Furthermore, the tape system utilized in apparatus 10 and the methods according to the teachings of the present invention only requires one manual step to load an entire spool of arrays. Conventional single plate real time PCR systems either require manual loading or a robotic autoloader, both of which added costs avoided according to the teachings of the present invention.

Since carrier tape 20 can be mounted on spool 40, much less physical space is required utilizing apparatus 10 and the methods of the present invention. A similar throughput using conventional 100 single plate real time PCR systems would require much more lab space than a single tape system utilized in apparatus 10 and the methods according to the teachings of the present invention.

Additionally, conventional current real time PCR systems require a lot of electricity per array, because of the thermal energy required to be transferred into and out of the plate. The tape based system utilized in apparatus 10 and the methods according to the teachings of the present invention will use much less energy per array.

It should be appreciated that apparatus 10 and the methods of the present invention allow reading fluorescence while the carrier tape 20 is surrounded by the fluid thermal media. An end point read can still be performed, if desired, utilizing apparatus 10 and the methods according to the teachings of the present invention. Also, apparatus 10 and the methods of the present invention can be utilized to perform real time readings of single temperature incubation chemistries. Furthermore, as both water and air can be utilized as the fluidic thermal media, both wet and dry incubation can be performed in apparatus 10 utilizing the preferred methods of the present invention.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

The invention claimed is:

1. Method for detection comprising:
   providing a fluid thermal media in a first tank, with all of the fluid thermal media in the first tank under temperature control different than outside of the first tank;
   providing a fluid thermal media in a second tank with all of the fluid thermal media of the second tank under temperature control different than the temperature control of the fluid thermal media in the first tank and different than outside the first and second tanks;

providing a carrier including regions containing contents with the carrier wound on and extending between first and second spools;

moving the carrier wound on and extending between the first and second spools from outside the first tank into the first tank and submerging the carrier wound on and extending between the first and second spools into the fluid thermal media of the first tank with the contents contained in the carrier undergoing a reaction while being submerged;

winding the carrier between the first and second spools with the carrier extending between the first and second spools while in the first tank, with submerging the carrier including submerging the first and second spools with the carrier extending therebetween in the fluid thermal media of the first tank; and detecting a condition of the contents in the regions of the carrier while the contents are submerged in the fluid thermal media of the first tank and while the contents are located intermediate the first and second spools, with submerging the carrier including submerging the carrier in the fluid thermal media of the second tank after the carrier is removed from the fluid thermal media of the first tank.

2. The method of claim 1 with detecting the condition comprising detecting the condition with a detector, with the method further comprising:

providing a guide mechanism intermediate the first and second spools and mounting the detector, with submerging the carrier including extending the carrier over the detector mounted to the guide mechanism with an obtuse angle being defined in the carrier by the guide mechanism intermediate the first and second spools.

3. The method of claim 1 wherein submerging the first and second spools comprises plunging the first and second spools with the carrier extending therebetween multiple times in opposite directions in the fluid thermal media of the first tank.

4. The method of claim 1 further comprising:

providing a read head including first and second spindles and mounting the detector;

loading the first and second spools in a load station outside of the first tank;

moving the read head to receive the first and second spools located in the load station on the first and second spindles, with submerging the carrier comprising moving the read head with the first and second spools received on the first and second spindles from the load station and into the first tank;

moving the read head with the first and second spools received on the first and second spindles from the first tank to an unload station after detecting the condition of the carrier and the contents in the wells; and moving the read head from the unload station with the first and second spools removed from the first and second spindles.

5. The method of claim 1 wherein detecting the condition comprises detecting the condition with a time-resolving photometer measuring fluorescence.

6. The method of claim 1 wherein the fluid thermal media in at least one of the first and second tanks is water.

7. The method of claim 1 wherein the fluid thermal media in at least one of the first and second tanks is air, with the method further comprising blowing the air to increase convection.

8. The method of claim 1 wherein winding the carrier comprises winding a carrier tape having the regions in a form of wells.

9. The method of claim 8 wherein submerging the carrier tape comprises moving the carrier tape including the wells in an array having rows and columns with the carrier tape being moved in a direction parallel to the rows, with detecting the condition comprising submerging a multi-channel detector having at least one channel per row of the array of wells.

10. Apparatus for detection comprising, in combination: a first tank containing a fluid thermal media with all of the fluid thermal media in the first tank under temperature control different than outside the first tank, with the first tank defining a volume having an opening; a second tank containing a fluid thermal media, with all of the fluid thermal media of the second tank under temperature control different than the temperature control of the fluid thermal media of the first tank and outside the first and second tanks, with the volume receiving a carrier spaced from the opening, with the carrier including regions containing contents, a head moveable into and out of the volume of the first tank through the opening, and a detector detecting a condition of the contents in the regions while the regions are received in the volume; first and second spools rotatably mounted to the head, with the detector located intermediate the first and second spools, with the carrier extending between the first and second spools, with the head and the first and second spools moveable from outside the first tank into the volume of the first tank through the opening.

11. The apparatus of claim 10 wherein the detector is in a form of a time-resolving photometer measuring fluorescence.

12. The apparatus of claim 10 further comprising, in combination: a load station holding the first and second spools removed from the head, with the load station located outside of the first tank; an unload station holding the first and second spools removed from the head, with the unload station located outside of the first tank; and a transfer mechanism moving the head from the load station to the first tank and from the first tank to the unload station.

13. The apparatus of claim 10 wherein the fluid thermal media is water.

14. The apparatus of claim 10 wherein the fluid thermal media is air, with the apparatus further comprising a blower blowing the air.

15. The apparatus of claim 10 wherein the head mounts the detector, with the detector located intermediate the first and second spools.

16. The apparatus of claim 15 further comprising, in combination: a guide mechanism mounted to the head intermediate the first and second spools, with the detector mounted to the guide mechanism, with tangents from the first and second spools to the guide mechanism defining an obtuse angle at the guide mechanism.

17. The apparatus of claim 10 wherein the head is adapted to carry the carrier in a form of a carrier tape with the regions in a form of wells.

18. The apparatus of claim 17 wherein the detector is a multi-channel detector, with the carrier tape extending between the first and second spools in a direction and including the wells arranged in an array having rows and columns, with the plurality of rows parallel to the direction, with the multi-channel detector including at least one channel per row of the array of wells.

19. Method for detection comprising:

providing a fluid thermal media in a first tank, with all of the fluid thermal media in the first tank under temperature control different than outside of the first tank;

providing a fluid thermal media in a second tank with all of the fluid thermal media in the second tank under temperature control different than the temperature control of the fluid thermal media in the first tank and outside the first and second tanks;

submerging a carrier including regions containing contents in the fluid thermal media of the first tank with the contents undergoing a reaction while being submerged;

submerging a detector in the fluid thermal media of the first tank for detecting a condition of the contents in the regions of the carrier while the contents are submerged in the fluid thermal media of the first tank;

submerging the carrier in the fluid thermal media of the second tank after the carrier is removed from the fluid thermal media of the first tank; and submerging the detector in the fluid thermal media of the second tank for detecting the condition of the contents in the regions of the carrier while the contents are submerged in the fluid thermal media of the second tank and after the detector is removed from the fluid thermal media of the first tank.

20. The method of claim 19 wherein submerging the carrier comprises submerging a head carrying the carrier and mounting the detector.

21. Apparatus for detection comprising a first tank containing a fluid thermal media, with all of the fluid thermal media in the first tank under temperature control different than outside of the first tank, with the first tank defining a volume having an opening, with the volume receiving a carrier spaced from the opening, with the carrier including regions containing contents, a second tank containing a fluid thermal media with all of the fluid thermal media in the second tank under temperature control different than the temperature control of the fluid thermal media in the first tank and outside the first and second tanks, with the second tank defining a volume having an opening, with the volume of the second tank receiving the carrier spaced from the opening of the second tank, and a detector detecting a condition of the contents in the regions; a read head mounting the detector, with the read head moveable into and out of the volume of the first tank through the opening of the first tank and moveable into and out of the volume of the second tank through the opening of the second tank.

22. The apparatus of claim 21 wherein the read head is adapted to carry the carrier with the detector.

* * * * *